US010765368B2

(12) United States Patent
Chang

(10) Patent No.: US 10,765,368 B2
(45) Date of Patent: Sep. 8, 2020

(54) WEARABLE DEVICES CONFIGURED FOR FACILITATING DIAGNOSIS AND/OR ASSESSMENT OF PULMONARY DISEASES, AND CORRESPONDING METHODS

(71) Applicant: LOS ANGELES BIOMEDICAL RESEARCH INSTITUTE AT HARBOR-UCLA MEDICAL CENTER, Torrance, CA (US)

(72) Inventor: Ruey-Kang Chang, Diamond Bar, CA (US)

(73) Assignee: LOS ANGELES BIOMEDICAL RESEARCH INSTITUTE AT HARBOR-UCLA MEDICAL CENTER, Torrance, CA (US)

( * ) Notice: Subject to any disclaimer, the term of this patent is extended or adjusted under 35 U.S.C. 154(b) by 1349 days.

(21) Appl. No.: 14/869,584

(22) Filed: Sep. 29, 2015

(65) Prior Publication Data

US 2016/0095549 A1    Apr. 7, 2016

Related U.S. Application Data

(60) Provisional application No. 62/059,722, filed on Oct. 3, 2014.

(51) Int. Cl.
*A61B 5/08* (2006.01)
*A61B 5/00* (2006.01)
(Continued)

(52) U.S. Cl.
CPC .......... *A61B 5/6833* (2013.01); *A61B 5/0002* (2013.01); *A61B 5/0823* (2013.01);
(Continued)

(58) Field of Classification Search
CPC ... A61B 5/6833; A61B 5/0823; A61B 5/1118; A61B 5/6822; A61B 5/113;
(Continued)

(56) References Cited

U.S. PATENT DOCUMENTS

2003/0199945 A1 * 10/2003 Ciulla .................. A61F 5/56
607/48
2005/0113646 A1    5/2005 Sotos et al.
(Continued)

OTHER PUBLICATIONS

International Preliminary Report on Patentability issued in corresponding PCT application No. PCT/US2015/052711 dated Apr. 13, 2017, 10 pages.

*Primary Examiner* — Christian Jang
(74) *Attorney, Agent, or Firm* — Pillsbury Winthrop Shaw Pittman LLP

(57) ABSTRACT

Exemplary implementations may provide objective, continuous, and clinically useful assessment of asthma control in subjects including young children using a device that is compact, non-intrusive, and simple. The device may include a water-resistant, flexible patch that can be comfortably worn for two weeks or more. In some implementations, the patch may resemble a Band-Aid® that is placed on the supra-sternal notch. The device may record respiratory sounds that can be analyzed to identify coughing and wheezing episodes. The device may operate in different modes including ones for assessment of nocturnal symptoms, exercise-induced asthma, and overall asthma control. The device may be useful for objectively assessing asthma control to aid clinical therapy, and for an improved way to diagnose exercise-induced asthma.

24 Claims, 6 Drawing Sheets

(51) Int. Cl.
*G16H 40/63* (2018.01)
*G16H 50/20* (2018.01)
*G16H 40/67* (2018.01)
*A61B 5/11* (2006.01)
*A61B 5/113* (2006.01)
*A61B 7/00* (2006.01)

(52) U.S. Cl.
CPC ............ *A61B 5/113* (2013.01); *A61B 5/1118* (2013.01); *A61B 5/6822* (2013.01); *A61B 7/003* (2013.01); *G16H 40/63* (2018.01); *G16H 40/67* (2018.01); *G16H 50/20* (2018.01); *A61B 2562/0204* (2013.01); *A61B 2562/0219* (2013.01); *A61B 2562/0271* (2013.01); *A61B 2562/164* (2013.01); *A61B 2562/18* (2013.01)

(58) Field of Classification Search
CPC ............ A61B 5/0002; A61B 2562/164; A61B 2562/204; A61B 2562/0271
See application file for complete search history.

(56) References Cited

U.S. PATENT DOCUMENTS

| | | | |
|---|---|---|---|
| 2005/0119711 A1* | 6/2005 | Cho ..................... | A61B 5/0205 607/42 |
| 2006/0155205 A1* | 7/2006 | Sotos .................. | A61B 5/4806 600/529 |
| 2009/0076346 A1 | 3/2009 | James et al. | |
| 2009/0076405 A1* | 3/2009 | Amurthur ............ | A61B 5/0002 600/529 |
| 2009/0088614 A1* | 4/2009 | Taub ................... | A61B 5/14532 600/316 |
| 2011/0213271 A1* | 9/2011 | Telfort .................. | A61B 7/003 600/586 |
| 2012/0041338 A1* | 2/2012 | Chickering, III ...... | A61B 5/415 600/575 |
| 2012/0065479 A1 | 3/2012 | Lahiji et al. | |
| 2012/0328606 A1* | 12/2012 | Gossage .......... | G01N 33/56972 424/133.1 |
| 2013/0317367 A1* | 11/2013 | Shuler ................ | A61B 5/14552 600/473 |

* cited by examiner

| Processor(s) | 400 |
|---|---|
| Computer Program Instructions | 402 |
| Recording Component | 404 |
| Modal Control Component | 406 |
| Power Management Component | 408 |
| Report Provisioning Component | 410 |
| Awake/Asleep Status Determination Component | 412 |
| Activity Level Determination Component | 414 |
| Poor Asthma Control Determination Component | 416 |
| Exercise-Induced Asthma Determination Component | 418 |
| Clinically-Significant Wheezing Determination Component | 420 |
| Cold-Air-Triggered Asthma Exacerbation Determination Component | 422 |
| Communications Component | 424 |

WEARABLE DEVICES CONFIGURED FOR FACILITATING DIAGNOSIS AND/OR ASSESSMENT OF PULMONARY DISEASES, AND CORRESPONDING METHODS

RELATED APPLICATIONS

The present application is related to U.S. Provisional Patent Application Ser. No. 62/059,722, filed Oct. 3, 2014, entitled "WEARABLE DEVICES CONFIGURED FOR FACILITATING DIAGNOSIS AND/OR ASSESSMENT OF PULMONARY DISEASES, AND CORRESPONDING METHODS", which is incorporated herein by reference in its entirety.

FIELD OF THE DISCLOSURE

This disclosure relates to wearable devices configured for facilitating diagnosis and/or assessment of pulmonary diseases, and corresponding methods.

BACKGROUND

Asthma may be considered one of the most preventable conditions necessitating frequent use of acute care services. To prevent hospitalizations and emergency department visits, it may be important for physicians to obtain an accurate assessment of a subject's asthma symptom control. A subject's perception and caretaker's (e.g., a parent or guardian) perception of asthma control of the subject may vary tremendously and frequently may not correlate with objective measures. In one study, 21% of parents described their children's asthma as very well controlled, and yet the child had visited the emergency room or required an acute outpatient visit for asthma in the last three months. With varying asthma phenotypes, poor asthma-control perception, and growing costs of asthma, adequate asthma-control measures are important.

SUMMARY

Exemplary implementations may provide objective, continuous, and clinically useful assessment of asthma control in subjects including young children using a device that is compact, non-intrusive, and simple. The device may include a water-resistant, flexible patch that can be comfortably worn for two weeks or more. In some implementations, the patch may resemble a Band-Aid® that is placed on the supra-sternal notch. The device may record respiratory sounds that can be analyzed to identify coughing and wheezing episodes. The device may operate in different modes including ones for assessment of nocturnal symptoms, exercise-induced asthma, and overall asthma control. The device may be useful for objectively assessing asthma control to aid clinical therapy, and for an improved way to diagnose exercise-induced asthma.

Indeed, one aspect of the disclosure relates to a wearable device configured for facilitating diagnosis and/or assessment of a pulmonary disease. The device may include a flexible patch having a skin contact surface configured to contact human skin. The device may include a water-resistant enclosure disposed upon or within the patch. The device may include an acoustic sensor disposed within the enclosure. The acoustic sensor maybe configured to provide an acoustic signal conveying information associated with internal respiratory sounds. The acoustic sensor may include a contact accelerometer configured to sense tissue vibration. The device may include a non-transitory computer-readable storage medium disposed within the enclosure. The storage medium may be configured to store information and provide access to the stored information. The device may include one or more processors disposed within the enclosure. The one or more processors may be configured by computer program instructions to record onto the storage medium information conveyed by one or more signals including the acoustic signal. The information may be analyzable to identify one or both of wheezing or coughing episodes.

Another aspect of the disclosure relates to a wearable device configured for facilitating diagnosis and/or assessment of a pulmonary disease. The device may include a flexible patch having a skin contact surface covered with a hypoallergenic adhesive configured to adhere to human skin. The device may include a water-resistant enclosure disposed upon or within the patch. The device may include an acoustic sensor disposed within the enclosure. The acoustic sensor may be configured to provide an acoustic signal conveying information associated with internal respiratory sounds. The device may include a muscle activity sensor disposed within the enclosure. The muscle activity sensor may be configured to provide a muscle activity signal conveying information associated with contraction of an accessory respiratory muscle. The device may include a non-transitory computer-readable storage medium disposed within the enclosure. The storage medium may be configured to store information and provide access to the stored information. The device may include one or more processors disposed within the enclosure. The one or more processors may be configured by computer program instructions to record onto the storage medium information conveyed by one or more signals including the acoustic signal and the muscle activity signal. The information may be analyzable to identify one or both of wheezing or coughing episodes. The one or more processors may be configured by computer program instructions to determine an occurrence of clinically significant wheezing. The determination may be based on information conveyed by the acoustic signal and the muscle activity signal.

Yet another aspect of the disclosure relates to a method for facilitating diagnosis and/or assessment of a pulmonary disease using a wearable device. The wearable device may include a flexible patch having a skin contact surface covered with a hypoallergenic adhesive configured to adhere to human skin and a water-resistant enclosure disposed upon or within the patch. The patch may be configured to be worn proximate to a suprasternal notch of a subject. The patch may be shaped to resemble an elongated adhesive bandage. The method may include obtaining an acoustic signal from an acoustic sensor disposed within the enclosure. The acoustic signal may convey information associated with internal respiratory sounds. The acoustic sensor may include a contact accelerometer configured to sense tissue vibration. The method may include obtaining a muscle activity signal from a muscle activity sensor disposed within the enclosure. The muscle activity signal may convey information associated with contraction of an accessory respiratory muscle. The method may include recording onto a non-transitory computer-readable storage medium disposed within the enclosure information conveyed by one or more signals including the acoustic signal and the muscle activity signal. The information may be analyzable to identify one or both of wheezing or coughing episodes. The method may include determining an occurrence of clinically significant wheezing. The determination may be based on information conveyed by the acoustic signal and the muscle activity signal.

Still another aspect of the disclosure relates to a method for treating a pulmonary disease. The method may include obtaining a diagnosis of the pulmonary disease using a wearable device. The device may include a flexible patch having a skin contact surface covered with a hypoallergenic adhesive configured to adhere to human skin. The device may include a water-resistant enclosure disposed upon or within the patch. The device may include an acoustic sensor disposed within the enclosure. The acoustic sensor may be configured to provide an acoustic signal conveying information associated with internal respiratory sounds. The acoustic sensor may include a contact accelerometer configured to sense tissue vibration. The device may include a non-transitory computer-readable storage medium disposed within the enclosure. The storage medium may be configured to store information and provide access to the stored information. The device may include one or more processors disposed within the enclosure. The one or more processors may be configured by computer program instructions to record onto the storage medium information conveyed by one or more signals including the acoustic signal. The information may be analyzable to identify one or both of wheezing or coughing episodes. The method may include administering a therapeutic agent effective in ameliorating the pulmonary disease.

These and other features, and characteristics of the present technology, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BRIEF DESCRIPTION OF THE DRAWINGS

FIG. 4 illustrates an exemplary processor included in the system of FIG. 1, in accordance with one or more implementations.

DETAILED DESCRIPTION

Figure 1:
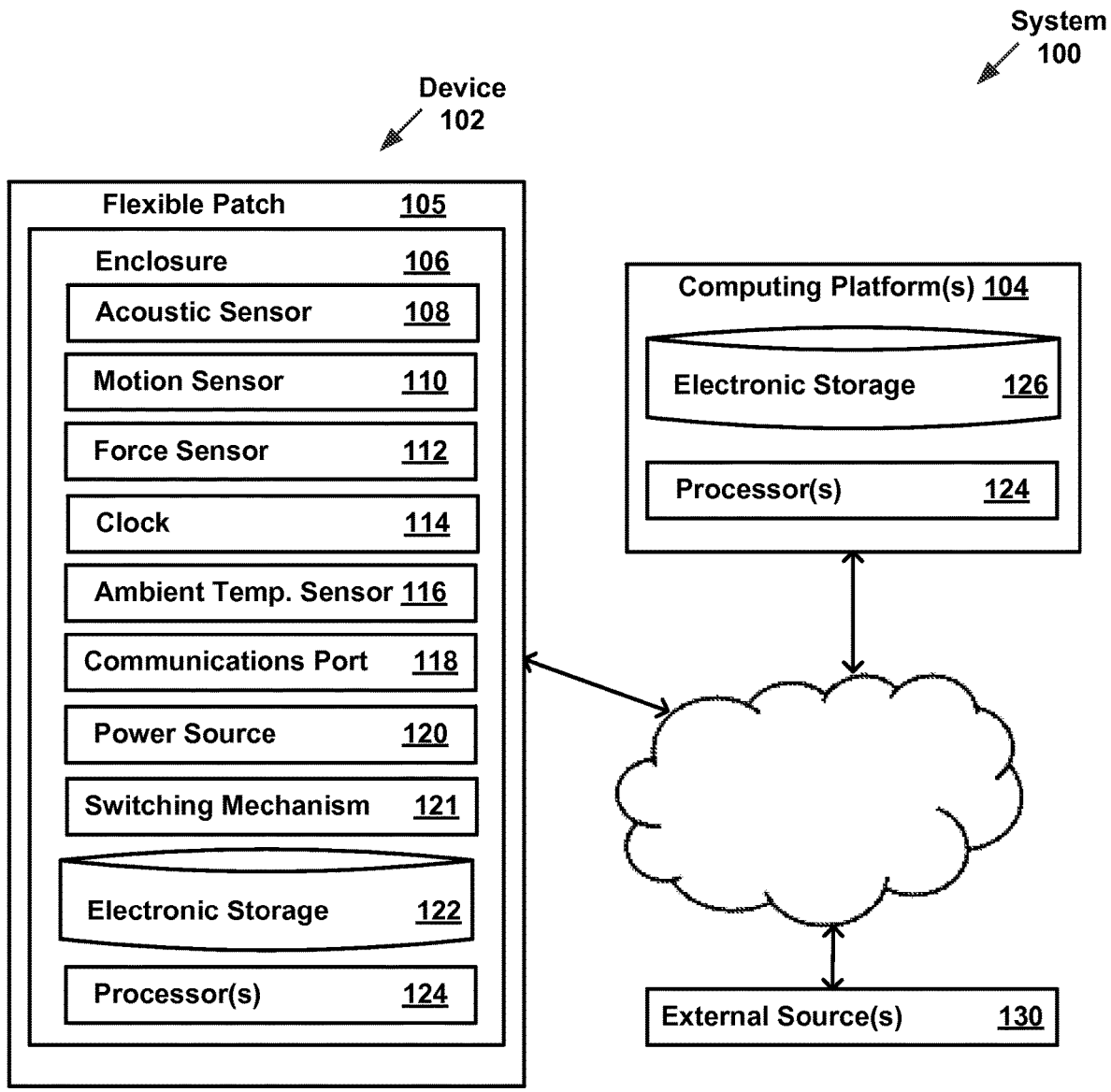
FIG. 1 illustrates a system configured for facilitating diagnosis and/or assessment of a pulmonary disease using a wearable device, in accordance with one or more implementations.

FIG. 1 illustrates a system 100 configured for facilitating diagnosis and/or assessment of a pulmonary disease using a wearable device 102, in accordance with one or more implementations. Although some implementations are described herein in the context of asthma, this is not intended to be limiting. For example, some implementations may be used for facilitating diagnosis and/or assessment of pulmonary disease including one or more of asthma, chronic obstructive pulmonary disease (COPD), emphysema, bronchitis, restrictive lung disease, pneumonia, atalectasis, consolidation, and/or other pulmonary diseases. In some implementations, system 100 may include a device 102, one or more computing platforms 104, and/or other components.

Figure 2:
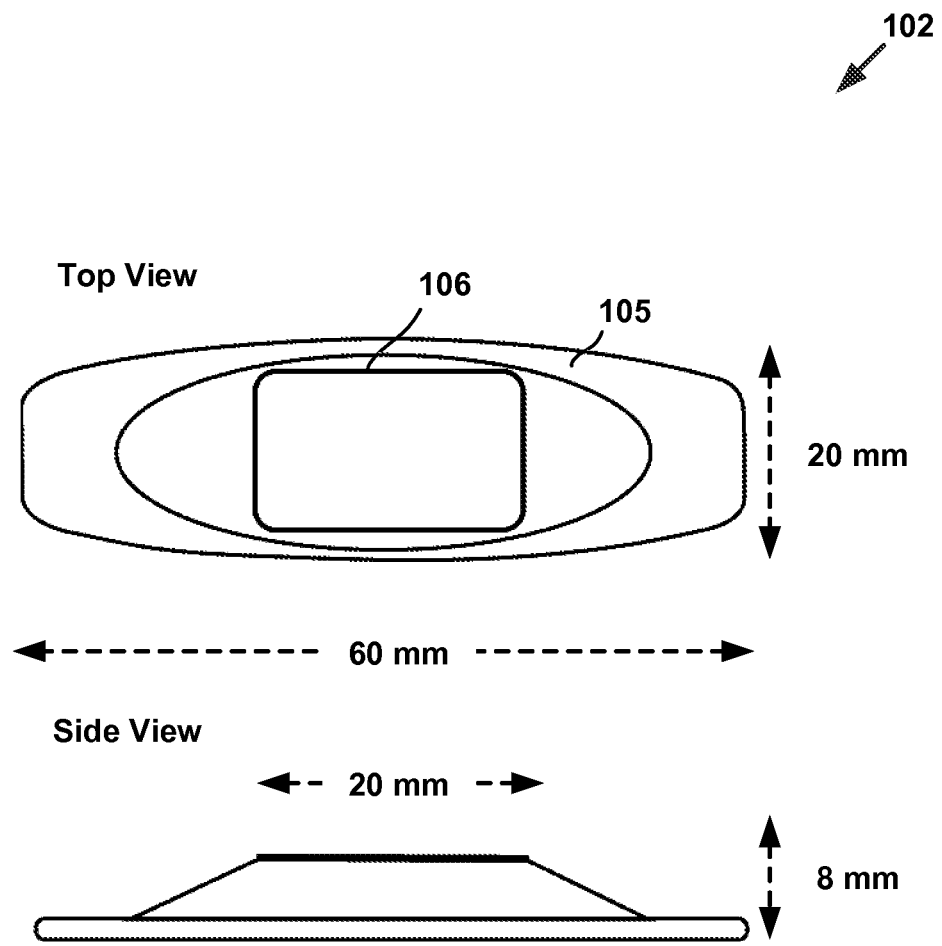
FIG. 2 illustrates an exemplary form factor of the wearable device, in accordance with one or more implementations.

The device 102 may include a flexible patch 105, an enclosure 106, and/or other components. In some implementations, device 102 may be referred to as a "wearable adherent device" or a "wearable adhesive device." The flexible patch 105 may comprise a flexible patch having a skin contact surface configured to contact human skin. In some implementations, flexible patch 105 may comprise an elongated shape reminiscent of typical adhesive bandages (e.g., a Band-Aid®). The flexible patch 105 may be sized approximately two by six centimeters. Other shapes and sizes are contemplated, and are within the scope of the disclosure. For example, the flexible patch 105 may be shaped as one or more of a V-shape, a U-shape, a circular or round shape (with or without lateral extensions), an elongated rectangular shape, and/or other shapes. The flexible patch 105 may be formed of a soft, stretchable foam patch. The enclosure 106 may comprise a water-resistant enclosure disposed upon or within the patch. This water resistance may allow a subject to bathe while still wearing device 102. In some implementations, enclosure 106 may be formed of a rigid or semi-rigid plastic or other material to protect its contents. FIG. 2 illustrates an exemplary form factor of device 102, in accordance with one or more implementations.

Figure 3:
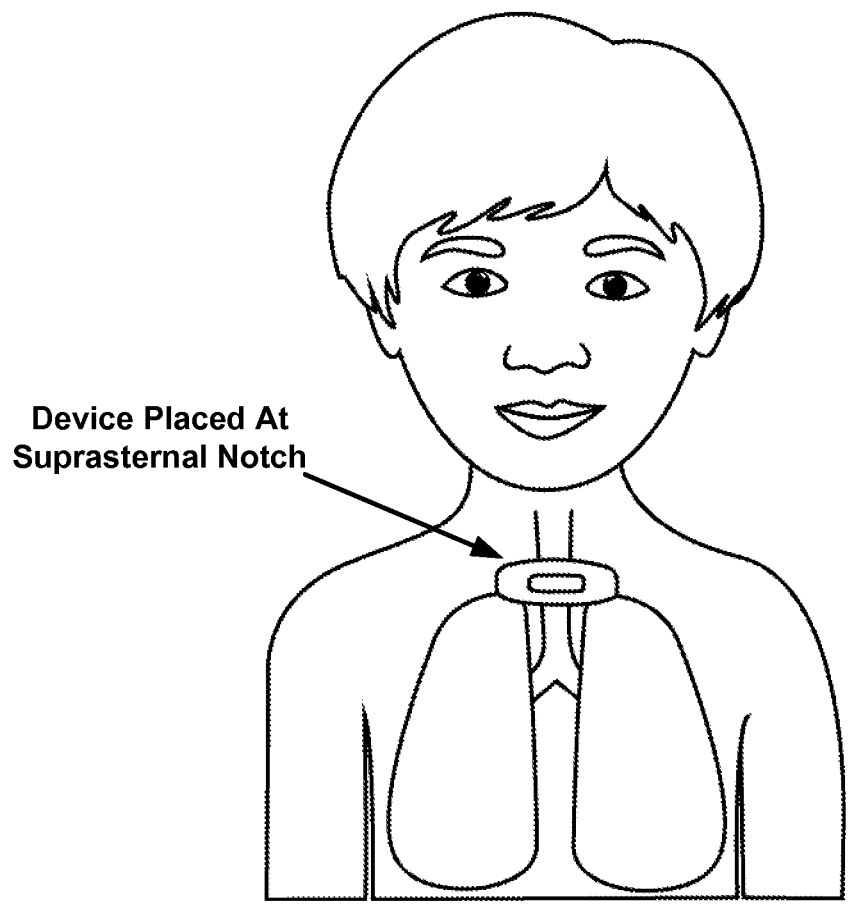
FIG. 3 illustrates an exemplary placement of the wearable device on a human subject, in accordance with one or more implementations.

FIG. 3 illustrates an exemplary placement of device 102 on a human subject, in accordance with one or more implementations. In some implementations, flexible patch 105 may be configured to be worn proximate to a suprasternal notch of a subject. The flexible patch may straddle over two sternocleidomastoid (SCM) muscles. Depending on the specific application, the location at which flexible patch 105 is to be worn may differ. For example, in some implementations, device 102 may be worn at upper sternum, right and/or left lung fields in front, right and/or left lung fields in back, the neck, upper chest, and/or other locations. In some implementations, device 102 may be worn at the lower chest in the front or in the back to detect abnormal breath sounds, such as wheezes, rhonchi or rales in the peripheral lungs.

Although system 100 is shown in FIG. 1 as including a single device 102, this is not intended to be limited as some implementations may include more than on device 102. For example, in some implementations, two or more devices the same as or similar to device 102 may be configured to be positioned at different locations on a subject (e.g., neck and upper lungs). In implementations including more than one device 102, those multiple devices 102 may be configured to communicate between each other.

In some implementations, the skin contact surface of flexible patch 105 may be covered with a hypoallergenic adhesive configured to adhere to human skin. Such adhesion may last for an entire measurement time period (e.g., one day, several days, one week, two weeks, and/or other durations). In some implementations, flexible patch 105 may comprise a strap used to secure flexible patch 105 in position on a subject. Other approaches for maintaining a position of flexible patch 105 relative to a subject are contemplated, and are within the scope of the disclosure.

Referring again to FIG. 1, enclosure 106 (and/or flexible patch 105) may carry, house, and/or enclose one or more of an acoustic sensor 108, a motion sensor 110, a muscle activity sensor 112, a clock 114, an ambient temperature sensor 116, a communications port 118, a power source 120, a switching mechanism 121, electronic storage 122, one or more processors 124, and/or other components. In some implementations, one or more of components 108, 110, 112, 114, 116, 118, 120, 121, 122, and/or 124 may be disposed outside of enclosure 106, and instead may be disposed on or within patch 105 or at a different location within system 100.

The acoustic sensor 108 may be configured to provide an acoustic signal conveying information associated with internal respiratory sounds. According to various implementations, acoustic sensor 108 may include a microphone configured to sense sound propagating in air, a contact accelerometer configured to sense tissue vibration, and/or other acoustic sensors. A contact accelerometer may provide certain advantages over some microphones including (1) reduced ambient noise; (2) improved signal-to-noise ratios, e.g., because tissue vibration may act as a low pass filter; (3) smaller physical dimensions, which may be important in wearable devices for young children; and (4) lower power consumption and data density, which are desirable for prolonged monitoring.

The motion sensor 110 may be configured to provide a motion signal conveying information associated with body motion of a subject wearing device 102. In some implementation, motion sensor 110 may include a tri-axial accelerometer and/or other sensor configured to detect motion and/or acceleration.

The muscle activity sensor 112 may be configured to provide a muscle activity signal conveying information associated with activity (e.g., contraction and/or retraction) of one or more muscles of a subject wearing device 102. In some implementations, the one or more muscles may include a sternocleidomastoid (SCM) muscle, other accessory respiratory muscles, and/or other muscles associated with respiration. The use of accessory respiratory muscles, such as the SCMs, may be a clinical sign called "retraction." Retraction may be indicative of significant distress from bronchoconstriction or wheezing. In some implementations, muscle activity sensor 112 may include a stretch sensor, a bend sensor, a tension sensor, a movement sensor, an electromyography (EMG) sensor, and/or other sensors configured to provide signals associated with muscle activity. In some implementations, muscle activity sensor 112 may be disposed at opposing ends of patch 105. The location at which muscle activity sensor 112 is disposed on patch 105 may be based on anatomical information such as muscle location.

The clock 114 may be configured to provide a clock signal conveying information associated with a time or duration. In some implementations, the clock signal may be used to provide a time stamp for other signals. The clock signal may convey information indicating how long device 102 has been worn. The clock signal may convey information indicating a time of day. In some implementations, clock 14 may be used to correlate information associated with wheezing and/or coughing to time of day. In some implementations, clock 114 may be configured to provide time stamps to some or all collected data so that data associated with different parameters can be synchronized.

The ambient temperature sensor 116 may be configured to provide a temperature signal conveying information associated with an ambient temperature (i.e., an air temperature in an environment surrounding a subject wearing device 102).

In some implementations, ambient temperature sensor 116 may include one or more of a thermometer, a thermocouple, a thermistor, and/or other sensors configured to detect temperature.

The communications port 118 may be configured to facilitate communication between one or more components of device 102, one or more components of computing platform(s) 104, and/or other components of system 100. The communications port 118 may facilitate wired or wireless communication. The communications port 118 may support one or more wired communications standards including Universal Serial Bus (USB), FireWire, and/or other wired communications standards. The communications port 118 may support one or more wireless communications standards including wireless wide area network (WWAN) (e.g., RTT, EDGE, LTE, WiMAX, and/or other WWAN standards), wireless local area network (WLAN) (e.g., Wi-Fi and/or other WLAN standards), wireless personal area network (WPAN) (e.g., Bluetooth, Wireless USB, ZigBee, and/or other WPAN standards), and/or other wireless communications standards. The communications port 118 may include radio-frequency identification (RFID).

The power source 120 may be configured to provide electrical power to one or more components of device 102. In some implementations, power source 120 may be configured to provide electrical power for an entire measurement time period (e.g., one week, two weeks, and/or other duration). In some implementations, power source 120 may be rechargeable. The power source 120 may include one or more of a battery, a capacitor, and/or other sources of electrical power.

The switching mechanism 121 may be configured to turn on or turn off electrical power to one or more components of device 102. In some implementations, device 102 may include a protective cover 125 configured to protect the skin contact surface of flexible patch 105 when device 102 is not in use. The switching mechanism 121 may be configured to activate one or more components of device 102 responsive to protective cover 125 being removed from the skin contact surface of patch 105. The switching mechanism 121 may be configured to deactivate one or more components of device 102 responsive to device 102 ceasing to be worn. By way of non-limiting example, switching mechanism 121 may include one or more of a magnetic switch, a mechanical switch, a sensor-triggered switch based on pre-defined parameters and/or thresholds, and/or other switching mechanisms.

As described above, device 102 may include electronic storage 122 and/or processor(s) 124. The electronic storage 122 may comprise non-transitory storage media that electronically stores information. Exemplary implementations of electronic storage 122 are described further herein. The processor(s) 124 may provide computing capabilities to device 102. Exemplary implementations of processor(s) 124 are described in connection with FIG. 4.

The computing platform(s) 104 may include electronic storage 126, one or more processors 128, and/or other components. The electronic storage 126 may comprise non-transitory storage media that electronically stores information. Exemplary implementations of electronic storage 126 are described further herein. The processor(s) 128 may provide computing capabilities to computing platform(s) 104. Exemplary implementations of processor(s) 128 are described in connection with FIG. 4. By way of non-limiting example, the given computing platform 104 may include one or more of a server computer, a desktop computer, a laptop computer, a handheld computer, a tablet computing platform, a NetBook, a Smartphone, and/or other computing platforms. In some implementations, a given computing platform 104 may be a mobile device configured to run an application by which device 102 can be interacted with by a user. Such interactions may include programming device 102, controlling a mode of operation of device 102, providing information to device 102, receiving information form device 102, and/or other interactions.

The computing platform(s) 104 may include communication lines, or ports to enable the exchange of information with a network and/or other computing platforms. Illustration of computing platform(s) 104 in FIG. 1 is not intended to be limiting. The computing platform(s) 104 may include a plurality of hardware, software, and/or firmware components operating together to provide the functionality attributed herein to computing platform(s) 104. For example, computing platform(s) 104 may be implemented by a cloud of computing platforms operating together as computing platform(s) 104.

In some implementations, device 102, computing platform(s) 104, and/or external resources 130 may be operatively linked via one or more electronic communication links. For example, such electronic communication links may be established, at least in part, via a network such as the Internet and/or other networks. It will be appreciated that this is not intended to be limiting, and that the scope of this disclosure includes implementations in which device 102, computing platform(s) 104, and/or external resources 130 may be operatively linked via some other communication media.

External resources 130 may include sources of information, hosts and/or providers of medical information outside of system 100, external entities participating with system 100, and/or other resources. In some implementations, some or all of the functionality attributed herein to external resources 130 may be provided by resources included in system 100.

Electronic storage 122 and/or electronic storage 126 may comprise non-transitory storage media that electronically stores information. The electronic storage media of electronic storage 122 may include one or both of system storage that is provided integrally (i.e., substantially non-removable) with device 102. The electronic storage media of electronic storage 126 may include one or both of system storage that is provided integrally (i.e., substantially non-removable) with computing platform(s) 104. Electronic storage 122 and/or electronic storage 126 may comprise removable storage that is removably connectable to device 102 and/or computing platform(s) 104, for example, a port (e.g., a USB port, a firewire port, etc.) or a drive (e.g., a disk drive, etc.). Electronic storage 122 and/or electronic storage 126 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 122 and/or electronic storage 126 may include one or more virtual storage resources (e.g., cloud storage, a virtual private network, and/or other virtual storage resources). Electronic storage 122 and/or electronic storage 126 may store software algorithms, information conveyed by one or more sensors including in device 102, information determined by processor(s) 124 and/or processor(s) 128, information received from device 102, information received from computing platform(s) 104, and/or other information that enables system 100 to function as described herein.

FIG. 4 illustrates an exemplary processor 400 included in system 100, in accordance with one or more implementations. The processor 400 may be the same as or similar to processor(s) 124 in device 102 and/or processor(s) 128 in computing platform(s) 104. The processor 400 may be configured by computer program instructions 402. The computer program instructions 402 may include one or more of a recording component 404, a modal control component 406, a power management component 408, a report provisioning component 410, an awake/asleep status determination component 412, an activity level determination component 414, a poor-asthma-control determination component 416, an exercise-induced asthma determination component 418, a clinically-significant wheezing determination component 420, a cold-air-triggered asthma exacerbation determination component 422, a communications component 424, and/or other components.

The recording component 404 may be configured to record information conveyed by one or more signals provided by device 102. As described above, those signals may include one or more of an acoustic signal provided by acoustic sensor 108, a motion signal provided by motion sensor 110, a muscle activity signal provided by muscle activity sensor 112, a clock signal provided by clock 114, a temperature signal provided by ambient temperature sensor 116, and/or other signals. Signals and/or information conveyed by signals may be synchronized based on the time at which they were acquired. Signals and/or information conveyed by signals may be time stamped based on the clock signal. The information recorded by recording component 404 may be analyzable to identify one or both of wheezing or coughing episodes. The recording component 404 may be configured to record information onto electronic storage 122, electronic storage 126, and/or other locations.

The modal control component 406 may be configured to control an operational mode of device 102. In some implementations, an operational mode may be customized by a user. In some implementations, an operational mode may be selected from among two or more preprogrammed operational modes of device 102. Examples of preprogrammed operational modes may include a nocturnal mode, an exercise mode, a 24-hour mode, a before/after mode, and/or other modes of operation. In the nocturnal mode, device 102 may be dormant during daytime and activated during nighttime. Daytime and nighttime may be defined by default time values or time values provided by a user. In the exercise mode, device 102 may be activated from a dormant state responsive to a level of exercise being detected. The device 102 may remain activated for a duration after the level of exercise ceases. The duration may be defined by a default duration value or a duration value provided by a user. In the 24-hour mode, device 102 may remain activated during all times device 102 is being worn. In the before/after mode, device 102 may be activated during specific times before and after a therapeutic treatment. The specific times may be defined by specific time values or specific time values provided by a user.

The power management component 408 may be configured to manage power usage by one or more components of device 102. In some implementations, power management component 408 may be configured to cause device 102 to record information during a fraction of the time during which device 102 is activated and/or being worn. By way of non-limiting example, the fraction of the time during which device 102 records may be defined as the first ten seconds of every minute, and/or some other periodic recordation. In some implementations, power management component 408 may be configured to initiate recording in response to a trigger. Examples of such a trigger may include one or more of detection of a clinically-significant wheeze or cough, detection of physical activity breaching a threshold, the subject wearing device 102 waking up, detection of an ambient temperature breaching a threshold, contraction of bilateral SCM muscles with inspiration, and/or other triggers.

The report provisioning component 410 may be configured to provide a report based on information recorded while device 102 is worn. The report may comprise one or more of a table, a graph, and/or other formats for conveying information. The report may convey one or more of: (1) an amount of time with nocturnal wheezing; (2) an amount of time with daytime wheezing; (3) an amount of sleep time with wheezing; (4) an amount of day time with wheezing; (5) an amount of nighttime coughs; (6) an amount of daytime coughs; (7) an amount of wheezing episodes during and/or after exercise; (8) an amount of moderate-vigorous physical activity (MVPA) associated with wheezing, (9) wheezing and/or coughing associated with exposure to cold ambient temperature, (10) wheezing and/or coughing associated with one or more triggers described in connection with power management component 408, and/or other information.

The awake/asleep status determination component 412 may be configured to determine whether a subject wearing the device is awake or sleeping. In some implementations, the determination may be based on information conveyed by one or more of the motion signal, postural signal, the clock signal, and/or other signals provided by sensors included in device 102. By way of non-limiting illustration, awake/asleep status determination component 412 may determine whether a subject wearing the device is awake or sleeping based on whether the subject is moving or still, a body position or orientation of the subject, a posture of the subject, whether it is daytime or nighttime, and/or other information.

The activity level determination component 414 may be configured to determine a current activity level of a subject wearing the device. In some implementations, the determination may be based on information conveyed by one or more of the motion signal, the clock signal, and/or other signals provided by sensors included in device 102. For example, activity level determination component 414 may determine a current activity level based on how much the subject is moving, a body position or orientation of the subject, a posture of the subject, what time the subject is scheduled to exercise (e.g., school recess, sports practice, and/or other scheduled exercise), and/or other information.

The poor-asthma-control determination component 416 may be configured to determine a presence of poor asthma control. In some implementations, the determination may be based on an indication of wheezing during exercise. The determination may be based on information conveyed by one or more of the acoustic signal, the motion signal, and/or other signals provided by sensors included in device 102. In one non-limiting illustration, poor-asthma-control determination component 416 may determine a presence of poor asthma control by correlating clinically-significant wheezing with periods of physical activity that breach a threshold.

The exercise-induced asthma determination component 418 may be configured to determine a presence of exercise-induced asthma. In some implementations, the determination may be based on an indication of wheezing after exercise. The determination may be based on one or more of information conveyed by the acoustic signal, the motion signal, and/or other signals provided by sensors included in device 102. For example, exercise-induced asthma determination component 418 may determine a presence of exercise-induced asthma by correlating clinically-significant wheezing with periods following physical activity that breached a threshold.

The clinically-significant wheezing determination component 420 may be configured to determine an occurrence of clinically significant wheezing. The determination being based on one or more of information conveyed by the acoustic signal, the muscle activity signal, and/or other signals provided by sensors included in device 102. Those skilled in the art will recognize that clinically-significant wheezing is distinct from wheezing in general. Children, for example, may wheeze frequently, but not all such wheezes may be clinically significant. In some implementations, clinically-significant wheezing determination component 420 may determine an occurrence of clinically-significant wheezing by correlating wheezing episodes (e.g., based on the acoustic signal) with contractions of the bilateral sternocleidomastoid (SCM) muscle (e.g., based on the muscle activity signal) with individual respiratory cycles.

The cold-air-triggered asthma exacerbation determination component 422 may be configured to determine a presence of cold air triggered asthma exacerbation. The determination may be based on information conveyed by one or more of the acoustic signal, the temperature signal, and/or other signals provided by sensors included in device 102. According to some implementations, cold-air-triggered asthma exacerbation determination component 422 may determine a presence of cold air triggered asthma exacerbation by correlating a period of wheezing and/or coughing with a period of time during which a subject wearing device 102 is in an environment with an ambient temperature that breaches a threshold.

The communications component 424 may be configured to facilitate communication between one or more of device 102, computing platform(s) 104, and/or other components of system 100. According to some implementations, communications component 424 may provide access by a user of a given computing platform 104 to information stored in device 102. The communications component 424 may allow a user of a given computing platform 102 to program an operational mode of device 102. The communications component 424 may facilitate a user interfacing with device 102 via a mobile app running on a given computing platform 104.

Processor(s) 400 may be configured to provide information processing capabilities in system 100 (e.g., in device 102 and/or computing platform(s) 104). As such, processor(s) 400 may include one or more of a digital processor, an analog processor, a digital circuit designed to process information, an analog circuit designed to process information, a state machine, and/or other mechanisms for electronically processing information. Although processor(s) 400 is shown in FIG. 4 as a single entity, this is for illustrative purposes only. In some implementations, processor(s) 400 may include a plurality of processing units. These processing units may be physically located within the same device (e.g., in device 102 and/or computing platform(s) 104), or processor(s) 400 may represent processing functionality of a plurality of devices operating in coordination (e.g., device 102 and/or computing platform(s) 104). The processor(s) may be configured to execute one of more components of computer program instructions 402 including one or more of components 404, 406, 408, 410, 412, 414, 416, 418, 420, 422, 424, and/or other components. Processor(s) 400 may be configured to execute one or more of components 404, 406, 408, 410, 412, 414, 416, 418, 420, 422, 424, and/or other components by software; hardware; firmware; some combination of software, hardware, and/or firmware; and/or other mechanisms for configuring processing capabilities on processor(s) 400. As used herein, the term "component" may refer to any component or set of components that perform the functionality attributed to a given component of computer program instructions 202. This may include one or more physical processors during execution of processor readable instructions, the processor readable instructions, circuitry, hardware, storage media, and/or any other components.

It should be appreciated that although components 404, 406, 408, 410, 412, 414, 416, 418, 420, 422, and 424 are illustrated in FIG. 1 as being implemented within a single processing unit, in implementations in which processor(s) 400 includes multiple processing units, one or more of components 404, 406, 408, 410, 412, 414, 416, 418, 420, 422, and/or 424 may be implemented remotely from the other components. The description of the functionality provided by the different components 404, 406, 408, 410, 412, 414, 416, 418, 420, 422, and/or 424 described below is for illustrative purposes, and is not intended to be limiting, as any of components 404, 406, 408, 410, 412, 414, 416, 418, 420, 422, and/or 424 may provide more or less functionality than is described. For example, one or more of components 404, 406, 408, 410, 412, 414, 416, 418, 420, 422, and/or 424 may be eliminated, and some or all of its functionality may be provided by other ones of components 404, 406, 408, 410, 412, 414, 416, 418, 420, 422, and/or 424. As another example, processor(s) 400 may be configured to execute one or more additional computer program instruction components that may perform some or all of the functionality attributed below to one of components 404, 406, 408, 410, 412, 414, 416, 418, 420, 422, and/or 424.

Figure 5:
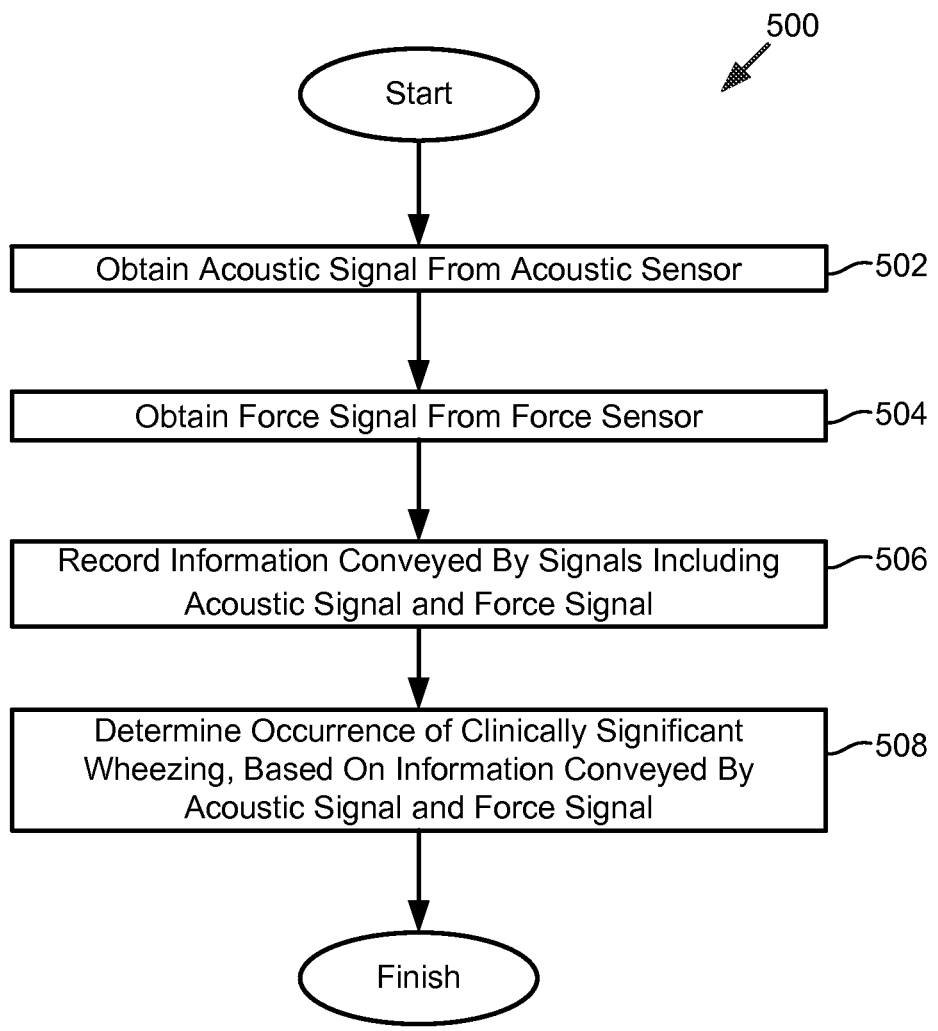
FIG. 5 illustrates a method for facilitating diagnosis and/or assessment of a pulmonary disease using a wearable device, in accordance with one or more implementations.
Figure 6:
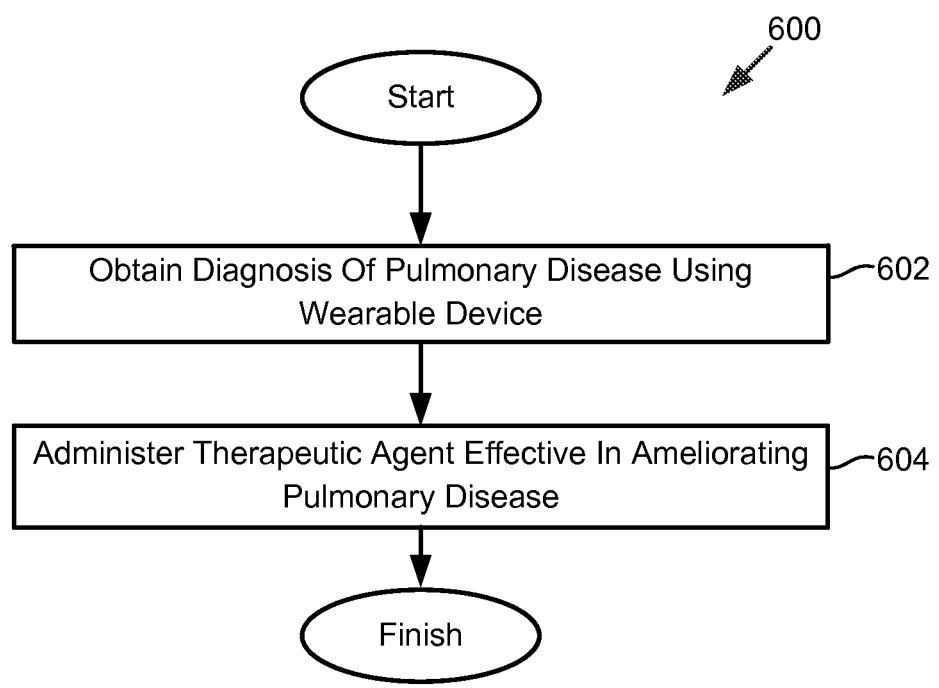
FIG. 6 illustrates a method for treating a pulmonary disease, in accordance with one or more implementations.

FIGS. 5 and 6 respectively illustrate method 500 and method 600, each being associated with device 102, in accordance with one or more implementations. The operations of method 500 and method 600 presented below are intended to be illustrative. In some implementations, method 500 and/or method 600 may be accomplished with one or more additional operations not described, and/or without one or more of the operations discussed. Additionally, the order in which the operations of method 500 and/or method 600 is illustrated in FIGS. 5 and 6 and described below is not intended to be limiting.

In some implementations, one or more operations of method 500 and/or method 600 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 500 and/or method 600 in response to instructions stored electronically on an electronic storage medium. The one or more processing devices may include one or more devices configured through hardware, firmware, and/or software to be specifically designed for execution of one or more of the operations of method 500 and/or method 600.

The method 500 illustrated in FIG. 5 is for facilitating diagnosis and/or assessment of a pulmonary disease using a wearable device (e.g., device 102), in accordance with one or more implementations. The wearable device may comprise a flexible patch having a skin contact surface covered with a hypoallergenic adhesive configured to adhere to human skin and a water-resistant enclosure disposed upon or within the patch. The patch may be configured to be worn proximate to a suprasternal notch of a subject. The patch may be shaped to resemble an elongated adhesive bandage.

At an operation 502, an acoustic signal may be obtained from an acoustic sensor (e.g., acoustic sensor 108. The acoustic sensor may be disposed within the enclosure of the wearable device. The acoustic signal may convey information associated with internal respiratory sounds. The acoustic sensor may include a contact accelerometer configured to sense tissue vibration. In some implementations, operation 502 may be performed by a processor configured to execute a recording component that is the same as or similar to recording component 404.

At an operation 504, a muscle activity signal may be obtained from a muscle activity sensor (e.g., muscle activity sensor 112). The muscle activity sensor may be disposed within the enclosure of the wearable device. The muscle activity signal may convey information associated with contraction of a sternocleidomastoid (SCM) muscle of a subject wearing the wearable device. In some implementations, operation 504 may be performed by a processor configured to execute a recording component that is the same as or similar to recording component 404.

At an operation 506, information conveyed by one or more signals including the acoustic signal and the muscle activity signal may be recorded onto a non-transitory computer-readable storage medium. The non-transitory computer-readable storage medium may be disposed within the enclosure of the wearable device. The information may be analyzable to identify one or both of wheezing or coughing episodes. In some implementations, operation 506 may be performed by a processor configured to execute a recording component that is the same as or similar to recording component 404.

At an operation 508, an occurrence of clinically significant wheezing may be determined. The determination may be being based on information conveyed by the acoustic signal and the muscle activity signal. In some implementations, operation 508 may be performed by a processor configured to execute a clinically-significant wheezing determination component that is the same as or similar to clinically-significant wheezing determination component 420.

The method 600 illustrated in FIG. 6 is for treating a pulmonary disease, in accordance with one or more implementations.

At an operation 602, a diagnosis of the pulmonary disease may be obtained using a wearable device and/or based on information obtained via the wearable device. In some implementations, the wearable device may comprise one or more of: a flexible patch having a skin contact surface covered with a hypoallergenic adhesive configured to adhere to human skin; a water-resistant enclosure disposed upon or within the patch; an acoustic sensor disposed within the enclosure, the acoustic sensor being configured to provide an acoustic signal conveying information associated with internal respiratory sounds, wherein the acoustic sensor is a contact accelerometer configured to sense tissue vibration; a non-transitory computer-readable storage medium disposed within the enclosure, the storage medium being configured to store information and provide access to the stored information; and one or more processors disposed within the enclosure, the one or more processors being configured by computer program instructions to record onto the storage medium information conveyed by one or more signals including the acoustic signal, the information being analyzable to identify one or both of wheezing or coughing episodes.

At an operation 604, a therapeutic agent effective in ameliorating the pulmonary disease may be administered. Examples of the therapeutic agent may include one or more therapeutic agents effective in ameliorating one or more of asthma, chronic obstructive pulmonary disease (COPD), emphysema, bronchitis, restrictive lung disease, pneumonia, atalectasis, consolidation, and/or other pulmonary diseases.

Although the present technology has been described in detail for the purpose of illustration based on what is currently considered to be the most practical and preferred implementations, it is to be understood that such detail is solely for that purpose and that the technology is not limited to the disclosed implementations, but, on the contrary, is intended to cover modifications and equivalent arrangements that are within the spirit and scope of the appended claims. For example, it is to be understood that the present technology contemplates that, to the extent possible, one or more features of any implementation can be combined with one or more features of any other implementation.

What is claimed is:

1. A wearable device configured for facilitating diagnosis and/or assessment of a pulmonary disease, the device comprising:
   a flexible patch having a single skin contact surface configured to contact human skin, wherein the skin contact surface is substantially continuous and planar such that the patch is configured to be worn proximate to a suprasternal notch of a human subject, and wherein the skin contact surface has a length configured to cause the patch to straddle two sternocleidomastoid muscles of the subject when the patch is worn by the subject;
   a water-resistant enclosure disposed upon or within the patch;
   an acoustic sensor disposed within the enclosure, the acoustic sensor being configured to provide an acoustic signal conveying information associated with internal respiratory sounds, wherein the acoustic sensor is a contact accelerometer configured to sense tissue vibration;
   a muscle activity sensor configured to provide a muscle activity signal conveying information associated with contraction of the sternocleidomastoid muscles, wherein portions of the muscle activity sensor are disposed at opposing ends of the flexible patch;
   a non-transitory computer-readable storage medium disposed within the enclosure, the storage medium being configured to store information and provide access to the stored information; and
   one or more processors disposed within the enclosure, the one or more processors being configured by computer program instructions to:
      record onto the storage medium information conveyed by the acoustic signal and the muscle activity signal, the information being analyzable to identify wheezing episodes and determine a presence of poor asthma control indicated by wheezing correlated to periods of physical activity, the determination being based on information conveyed by the acoustic signal and the muscle activity signal.

2. The device of claim 1, wherein the patch is shaped to resemble an elongated adhesive bandage.

3. The device of claim 1, further comprising a communications port disposed within the enclosure, the communications port being configured to facilitate communication between one or more components of the device and a computing platform that is physically separate and distinct from the device.

4. The device of claim 1, further comprising a power source disposed within the enclosure, the power source being configured to provide electrical power to one or more components of the device.

5. The device of claim 4, wherein the power source is configured to provide electrical power for more than two weeks.

6. The device of claim 1, wherein the skin contact surface of the patch is covered with a hypoallergenic adhesive configured to adhere to human skin.

7. The device of claim 6, further comprising a protective cover configured to protect the hypoallergenic adhesive covering the skin contact surface of the patch when the device is not in use.

8. The device of claim 7, further comprising a switching mechanism configured to activate one or more components of the device responsive to the protective cover being removed from the skin contact surface of the patch.

9. The device of claim 1, further comprising a switching mechanism configured to deactivate one or more components of the device responsive to the device ceasing to be worn.

10. The device of claim 1, wherein the one or more processors are further configured by computer program instructions to control an operational mode of the device, the operational mode being selected from among three preprogrammed operational modes of the device.

11. The device of claim 10, wherein one of the three preprogrammed operation modes comprises
   a before/after mode in which the device is activated during specific times before and after a therapeutic treatment, the specific times being defined by specific time values or specific time values provided by a user.

12. The device of claim 1, wherein the one or more processors are further configured by computer program instructions to cause the device to record information during a fraction of the time during which the device is activated.

13. The device of claim 12, wherein the fraction of the time during which the device records is defined as the first ten seconds of every minute.

14. The device of claim 1, wherein the one or more processors are further configured by computer program instructions to provide a report based on information recorded while the device is worn, the report comprising one or both of a table or a graph conveying one or more of:
   (1) an amount of time with nocturnal wheezing;
   (2) an amount of time with daytime wheezing;
   (3) an amount of sleep time with wheezing;
   (4) an amount of day time with wheezing;
   (5) an amount of wheezing episodes during and/or after exercise; or
   (6) an amount of moderate-vigorous physical activity (MVPA) associated with wheezing.

15. The device of claim 1, wherein the muscle activity sensor comprises a stretch sensor or a bend sensor.

16. The device of claim 1, further comprising an ambient temperature sensor disposed within the enclosure, the ambient temperature sensor being configured to provide a temperature signal conveying information associated with an ambient temperature.

17. The device of claim 16, wherein the one or more processors are further configured by computer program instructions to determine a presence of cold air triggered asthma exacerbation, the determination being based on information conveyed by the acoustic signal and the temperature signal.

18. The device of claim 1, wherein the one or more processors are further configured by computer program instructions to facilitate communication between the device and a computing platform that is physically separate and distinct from the device.

19. The device of claim 18, wherein the computing platform is a mobile device configured to run an application by which the device can be programmed.

20. The device of claim 1, wherein the pulmonary disease includes asthma.

21. A wearable device configured for facilitating diagnosis and/or assessment of a pulmonary disease, the device comprising:
- a flexible patch having a single skin contact surface, wherein the skin contact surface is covered with a hypoallergenic adhesive configured to adhere to human skin, wherein the skin contact surface is substantially continuous and planar such that the patch is configured to be worn proximate to a suprasternal notch of a human subject and wherein the skin contact surface has a length configured to cause the patch to straddle two sternocleidomastoid muscles of the subject when the patch is worn by the subject;
- a water-resistant enclosure disposed upon or within the patch;
- an acoustic sensor disposed within the enclosure, the acoustic sensor being configured to provide an acoustic signal conveying information associated with internal respiratory sounds;
- a muscle activity sensor, the muscle activity sensor being configured to provide a muscle activity signal conveying information associated with contraction of an accessory respiratory muscle, wherein portions of the muscle activity sensor are disposed at opposing ends of the flexible patch;
- a non-transitory computer-readable storage medium disposed within the enclosure, the storage medium being configured to store information and provide access to the stored information; and
- one or more processors disposed within the enclosure, the one or more processors being configured by computer program instructions to:
  - record onto the storage medium information conveyed by the acoustic signal and the muscle activity signal, the information being analyzable to identify wheezing;
  - determine an occurrence of clinically significant wheezing correlated to periods of physical activity, the determination being based on information conveyed by the acoustic signal and the muscle activity signal; and
  - determine a presence of poor asthma control based on the determination of clinically significant wheezing correlated to periods of physical activity.

22. The device of claim 21, wherein the acoustic sensor includes one or both of a microphone configured to sense sound propagating in air or a contact accelerometer configured to sense tissue vibration.

23. The device of claim 21, wherein the pulmonary disease includes asthma.

24. The device of claim 21, wherein the accessory respiratory muscle comprises the two sternocleidomastoid muscles.

* * * * *